United States Patent [19]
Knodel et al.

[11] Patent Number: 5,653,721
[45] Date of Patent: Aug. 5, 1997

[54] OVERRIDE MECHANISM FOR AN ACTUATOR ON A SURGICAL INSTRUMENT

[75] Inventors: Bryan D. Knodel; Ben Thompson, both of Cincinnati; Dale R. Schulze, Lebanon, all of Ohio

[73] Assignee: Ethicon Endo-Surgery, Inc., Cincinnati, Ohio

[21] Appl. No.: 545,296

[22] Filed: Oct. 19, 1995

[51] Int. Cl.[6] .................................................. A61B 17/08
[52] U.S. Cl. ............................................ 606/151; 227/175.1
[58] Field of Search ................................ 606/151, 142, 606/143, 205, 206, 207, 208, 147, 148; 227/175.1, 175.2, 175.3, 176.1, 177.1, 181.1, 182.1

[56] References Cited

U.S. PATENT DOCUMENTS

| | | | |
|---|---|---|---|
| 4,169,476 | 10/1979 | Hiltebrandt | 128/325 |
| 4,784,137 | 11/1988 | Kulik et al. | 128/334 |
| 5,009,661 | 4/1991 | Michelson | 606/170 |
| 5,040,715 | 8/1991 | Green et al. | 227/176 |
| 5,071,430 | 12/1991 | de Salis et al. | 606/219 |
| 5,190,203 | 3/1993 | Rodak | 227/175 |
| 5,300,082 | 4/1994 | Sharpe et al. | 606/147 |
| 5,307,976 | 5/1994 | Olson et al. | 227/178 |
| 5,425,745 | 6/1995 | Green et al. | 606/219 |
| 5,499,998 | 3/1996 | Meade | 606/207 |
| 5,562,699 | 10/1996 | Heimberger | 606/205 |

FOREIGN PATENT DOCUMENTS

| | | |
|---|---|---|
| 51-149985 | 5/1950 | Japan . |
| 728848 | 5/1980 | U.S.S.R. . |

*Primary Examiner*—Michael Buiz
*Assistant Examiner*—Tina T. D. Pham
*Attorney, Agent, or Firm*—Matthew S. Goodwin

[57] ABSTRACT

A surgical instrument which has override protection when excessively thick tissue is attempted to be clamped between opposed jaws of an end effector is disclosed. The instrument includes a frame, a shaft extending from the frame, an end effector connected to the shaft distal end which includes movable, opposed jaws for clamping tissue therebetween, a clamping trigger, a resilient spring element fixed to the trigger, an actuator which translates movement from the clamping trigger to the movable jaws for clamping tissue, and an engaging element which is biased by the spring element against the actuator. When routine forces are applied by the user as the clamping trigger is moved to clamp tissue between the jaws, the engaging element causes the actuator to move in a forward direction for corresponding movement of the jaws from an open to a closed position. If excessive loads are applied, then the resilient spring element is compressed, and the engaging element is correspondingly released from its engagement with the actuator. Accordingly, further movement of the clamping trigger will not cause further translation of the actuator in the forward direction. Therefore, excessive loads are prevented, and the component parts of the instrument will be prevented from breaking. The invention is also applicable to actuators used for other functions such as stapling and cutting tissue.

14 Claims, 7 Drawing Sheets

OVERRIDE MECHANISM FOR AN ACTUATOR ON A SURGICAL INSTRUMENT

BACKGROUND OF THE INVENTION

This invention relates to a surgical instrument which has an actuating trigger or lever to perform a desired function. More specifically, it relates to such an instrument which requires the user to squeeze or depress a trigger or lever with the hand to operate the instrument to perform a desired function.

Surgical instruments routinely incorporate a frame which houses a pistol grip trigger or lever. When the user squeezes the trigger, or depresses the lever, an "end effector" at the business end of the instrument is actuated to perform a desired surgical function. For example, the end effector may cause bodily tissue to be clamped, cut, fastened with staples, or all three of these.

A surgical instrument which has found widespread acceptance and use is the linear cutter, sometimes referred to as the endocutter when adapted for endoscopic surgical applications. A surgical cutter includes an end effector having opposed jaws movable relative to each other, one jaw containing an anvil and the other containing a cartridge housing a plurality of staples. Tissue is clamped between the jaws, and then staples are fired into the clamped tissue to fasten the tissue. As the staples are fired, a knife cuts the tissue between the vertical rows of staple lines. The end effector of a surgical cutter is actuated to perform these functions when a first trigger or lever is squeezed or depressed to clamp the tissue between the opposed jaws, and then a second trigger or lever is squeezed or depressed to fasten the tissue with staples and cut the tissue between the staple lines.

Of course, other surgical instruments having end effectors performing other functions are used or have been described for use in various medical and surgical procedures. These other instruments also require an actuating trigger or lever to manipulate the end effector.

When the trigger or lever of a surgical instrument is actuated to manipulate the end effector for performing a desired function, the user must apply force to cause the actuation by squeezing the trigger or depressing the lever against the frame of the instrument. The amount of force which the user must apply depends on whether the instrument can efficiently transfer that force from the frame to the end effector, and also on the particular function which the end effector is intended to carry out. Often, it may be difficult to transfer the force applied from the frame of the instrument to the end effector when the instrument is particularly adapted for endoscopic surgery. An endoscopic instrument typically has an elongated, small diameter shaft between the frame and the end effector. Therefore, the force applied when the trigger or lever is actuated must be transferred into and through the elongated shaft to the end effector, and this can sometimes result in undesired inefficiencies. In addition, the clamping of tissue and the firing of staples into tissue also requires the delivery of high forces to the end effector. As the thickness of the tissue increases, the amount of force necessary to clamp and fasten tissue likewise increases.

In some situations, particularly those involving the use of endoscopic cutters to clamp, fasten and cut tissue, the forces generated when the user squeezes the trigger or depresses the lever to perform these functions may be excessive. In other words, the forces generated to manipulate the end effector in a desired way under certain "loading" conditions may exceed the design specifications of one or more of the various components of the instrument. Unfortunately, when this occurs, those components for which the design specifications have been exceeded may break. Consequently, the instrument fails for its intended purpose. Not only can this occurrence be simply troublesome and inconvenient because the surgeon unexpectedly needs to replace the broken instrument with a working one, but also potentially dangerous. The surgery may have proceeded to a particularly delicate point where easy replacement of the instrument is impractical, or the tissue may have been damaged because it was inadvertently manipulated in an improper way.

Actuating mechanisms have been described which have not fully addressed the situation which may arise in surgery where excessive forces are encountered. Co-pending application Ser. No. 08/235,070, filed Apr. 29, 1994, describes an endoscopic surgical cutter which includes a clamping trigger on a pistol grip handle. If tissue beyond a preset range of thickness is inserted between the jaws for clamping, the clamping trigger will not latch into its fully actuated position when the handle is squeezed. Instead, the latch mechanism cannot be activated, and the clamping trigger will return to its normal unactuated position to prevent the user from firing staples into the tissue. However, if excessively thick tissue is placed between the jaws, then it is still possible for the user to apply undue force to the clamping trigger resulting in a failure of one or more parts of the instrument.

Since the surgical instruments currently available in commerce or described in the literature do not fully address the potential for applying excessive force to an actuating trigger or lever of the instrument to cause an instrument failure, a mechanism which prevents the application of excessive force to prevent damage to the instrument, and more importantly, to the patient, is highly desirable.

SUMMARY OF THE INVENTION

The invention is a surgical instrument capable of clamping bodily tissue during a surgical procedure. The instrument comprises a frame and a shaft extending from the frame. The shaft has a distal end, and an end effector is connected to the shaft distal end. The end effector includes first and second opposed jaws which are movable from an open position where the jaws are spaced apart from each other to a closed position for clamping the tissue between the jaws.

The instrument further comprises a clamping trigger movably mounted to the frame. The clamping trigger has a gripping portion at a first end of the trigger and a mounting portion at an opposite end. The clamping trigger is movable from a first position to a second position. A resilient spring element is fixed to the mounting portion of the clamping trigger. An actuator can reciprocate within the frame in response to movement of the clamping trigger. The actuator is also operatively connected to the jaws through the shaft. An engaging element is attached to the resilient spring element fixed to the mounting portion of the clamping trigger. The engaging element is releasably biased by the resilient spring element against the actuator.

Accordingly, when the engaging element is biased against the actuator, movement of the clamping trigger from its first to second positions causes the actuator to reciprocate in a forward direction, consequently moving the jaws from their open to closed positions. Correspondingly, when the engaging element is released by the resilient spring element from biasing against the actuator, movement of the clamping trigger from the first to second positions no longer causes the actuator to reciprocate in a forward direction for corresponding movement of the jaws.

Significantly, the use of the spring element to create the resilient bias of the engaging element against the actuator provides an outstanding mechanism to prevent overloading of the component parts of the instrument when excessively thick tissue is attempted to be clamped between the jaws. When excessively thick tissue is placed between the jaws, the force of the engaging element against the actuator as the clamping trigger is moved to clamp the tissue will cause the resilient spring element to compress. When it compresses, the engaging element, which under normal loading conditions is biased against the actuator, is released from its engagement with the actuator. Accordingly, an excessive load cannot be exerted from the clamping trigger to the actuator, and the design limitations of the various component parts of the instrument correspondingly will not be exceeded.

Notably, the surgical instrument of this invention which incorporates the resilient spring element to prevent overloading the components of the instrument represents a "fail soft" mechanism. In other words, the user of the instrument will automatically fail to clamp excessively thick tissue between the jaws in a manner which will cause the instrument to break during surgery. When the excessively thick tissue is removed from the jaws, and consequently the overload condition is removed, the clamping trigger is reset so that the resilient spring element once again biases the engaging element against the actuator. In this way, when acceptably thick tissue is placed between the jaws, movement of the clamping trigger will close the jaws to clamp the tissue.

Another benefit of this invention is that unlike certain alternative approaches for providing protection against overload, the protection provided by the instrument of this invention is immediate. In contrast, alternative instruments have incorporated bendable trigger handles which "bottom out" against a stop near the end of their intended stroke of operation before a potential overload is avoided.

The instrument of this invention can be used in any surgical procedure where it is desired to clamp bodily tissue between opposed jaws of the end effector of the instrument. Alternatively, the instrument can be used for a wide range of applications where the "fail soft" mechanism can be applied to not only the clamping trigger, but also the firing trigger of a surgical fastening instrument to prevent excessive loads when, for example, staples are fired into tissue or the tissue is cut with a knife blade. The instrument of this invention can be used for conventional, open surgical procedures, as well as endoscopic surgical procedures.

DETAILED DESCRIPTION OF THE PREFERRED EMBODIMENT

Figure 1:
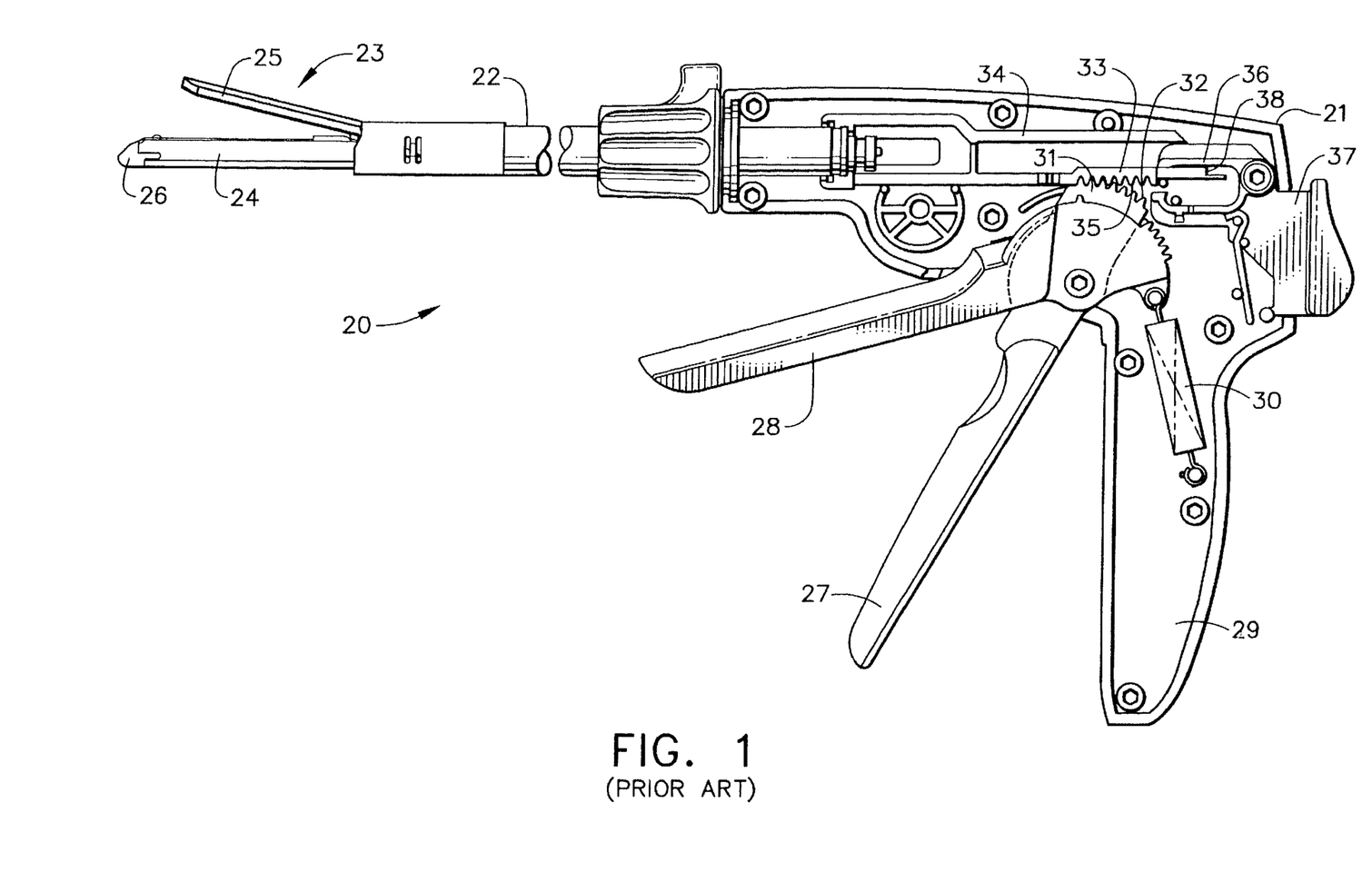
FIG. 1 is a side elevation of a conventional surgical instrument of the prior art in the form of an endoscopic linear cutter. One-half of the frame assembly is removed to expose the interior components of the cutter. The clamping trigger is in its first open position, and accordingly, the end effector which includes the mutually opposed jaws is its open position.
Figure 2:
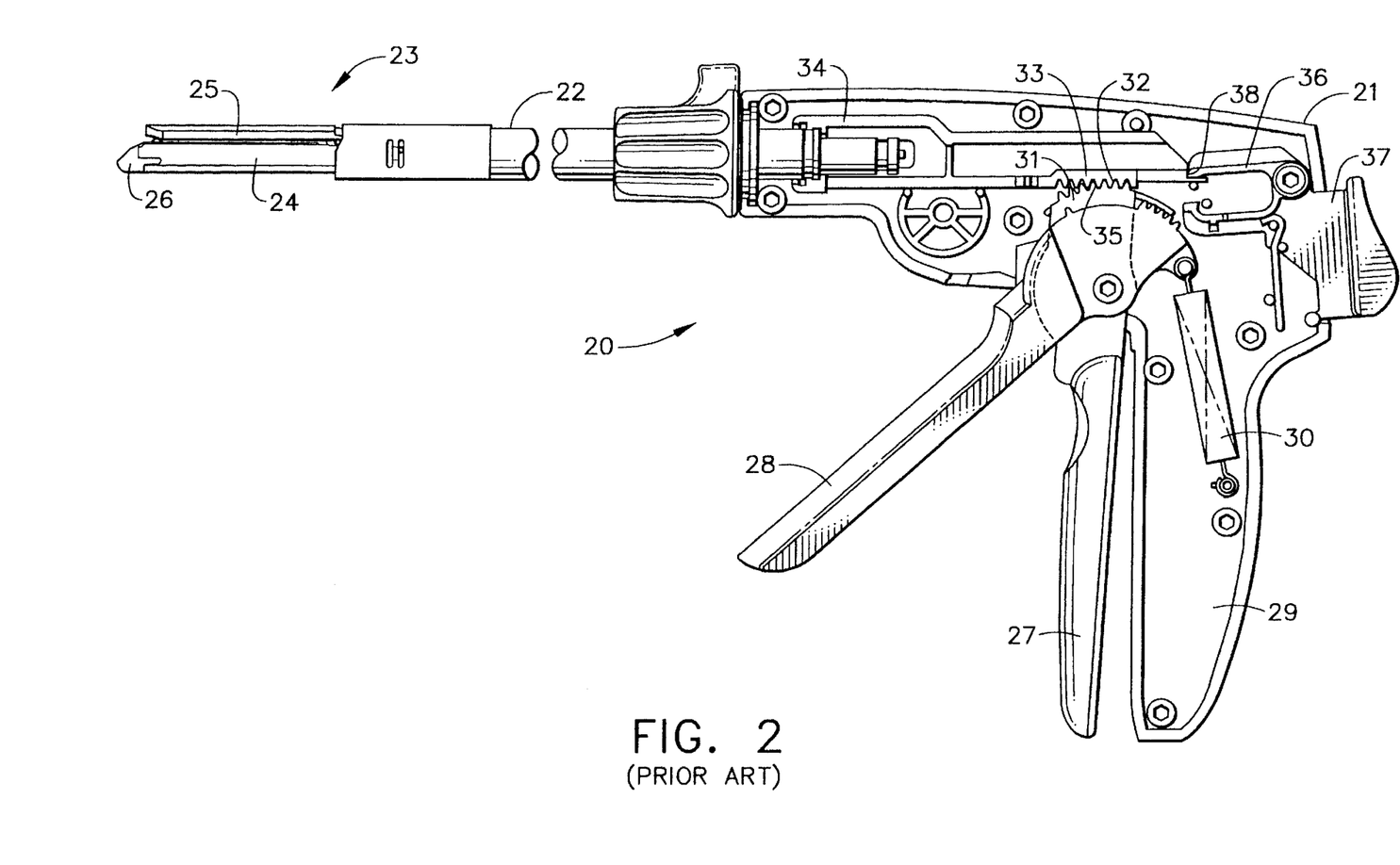
FIG. 2 is a side elevation similar to that illustrated in FIG. 1, except that the clamping trigger has been moved to its second closed position. Accordingly, the mutually opposed jaws of the end effector are in their closed position for clamping tissue therebetween.

FIGS. 1 and 2 represent an illustration of an endoscopic linear cutter in its unclamped and clamped positions, respectively. This endoscopic linear cutter, frequently referred to as an "endocutter", is described in detail in commonly assigned, copending application Ser. No. 08/191,412, filed Mar. 18, 1994. The illustrations of the prior art endocutter are noteworthy because substantially similar components which enable the operation of this particular endocutter can be used in connection with the surreal instrument of this invention. Indeed, in the most preferred embodiment, the surgical instrument of this invention is an endocutter which has the same basic components as shown in FIGS. 1 and 2.

The prior art endocutter 20 illustrated in FIGS. 1 and 2 has a frame 21 for readily gripping the instrument. Extending from the frame is an elongated, tubular shaft 22. At the distal end of the shaft, an end effector 23 including first and second mutually opposed jaws 24 and 25, respectively, is attached. The first jaw is in the shape of a channel for releasably receiving a staple cartridge 26. The second jaw is an anvil upon which staples (not shown) from the staple cartridge are formed. Clamping and firing triggers 27 and 28, respectively, are pivotably mounted to the frame. The frame includes a palm grip handle 29 for facilitating the gripping of the endocutter. When the jaws of the end effector are open for receiving bodily tissue between them, the clamping trigger is positioned at a first position spaced from the palm grip handle as depicted in FIG. 1. When the user squeezes the clamping trigger to rotate this trigger toward the palm grip handle, the clamping trigger will position itself at a final position adjacent the palm grip handle. In this position the anvil has pivoted toward the cartridge so that the jaws are in a closed position for clamping the tissue as depicted in FIG. 2. Once the tissue has been clamped between the jaws, the firing trigger has moved into position so that the user can squeeze this trigger for firing the staples from the cartridge through the tissue for formation against the anvil.

When the user squeezes the clamping trigger and overcomes the bias created from the frame assembly spring 30, a clamping trigger pinion 31 with a set of pinion gear teeth 32 engage a rack 33 on an actuator 34 with a mating set of gear teeth 35. The pinion translates the rotational movement of the clamping trigger as it is squeezed toward the palm grip handle to reciprocating movement of the actuator. The actuator 34 correspondingly moves in a forward, longitudinal direction. It in turn moves the shaft 22 forwardly. The shaft acts as a closure element to facilitate the movement of the anvil toward the staple cartridge 26. Once the clamping trigger has been moved from its first spaced apart position to its second position adjacent the palm grip handle, the upper arm 36 of the interlock assembly 37 pivots counterclockwise and is positioned on an actuator detent 38 to prevent the clamping trigger from returning to its first, unbiased spaced apart position. As shown in FIG. 2, the firing trigger is now in a position to be squeezed to fire staples into the tissue, and to cut the fastened tissue between rows of staples with a knife blade (not shown).

Figure 3:
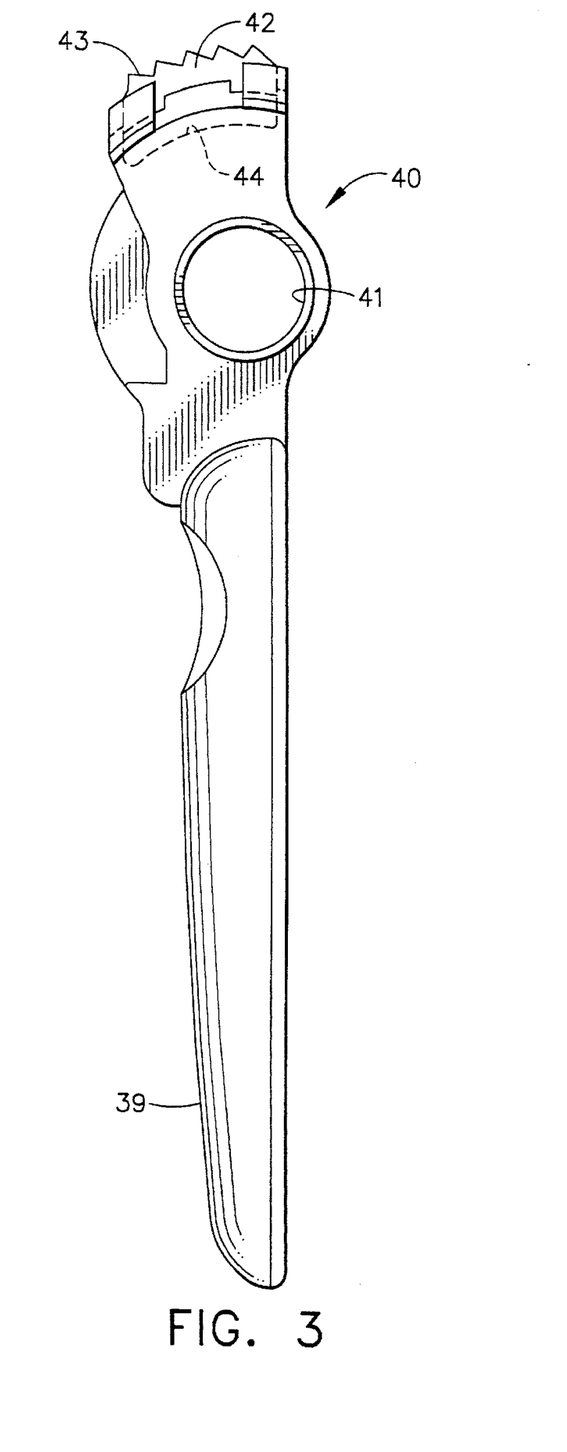
FIG. 3 is a side elevation of the clamping trigger of a surgical instrument constructed in accordance with a preferred embodiment of this invention.
Figure 4:
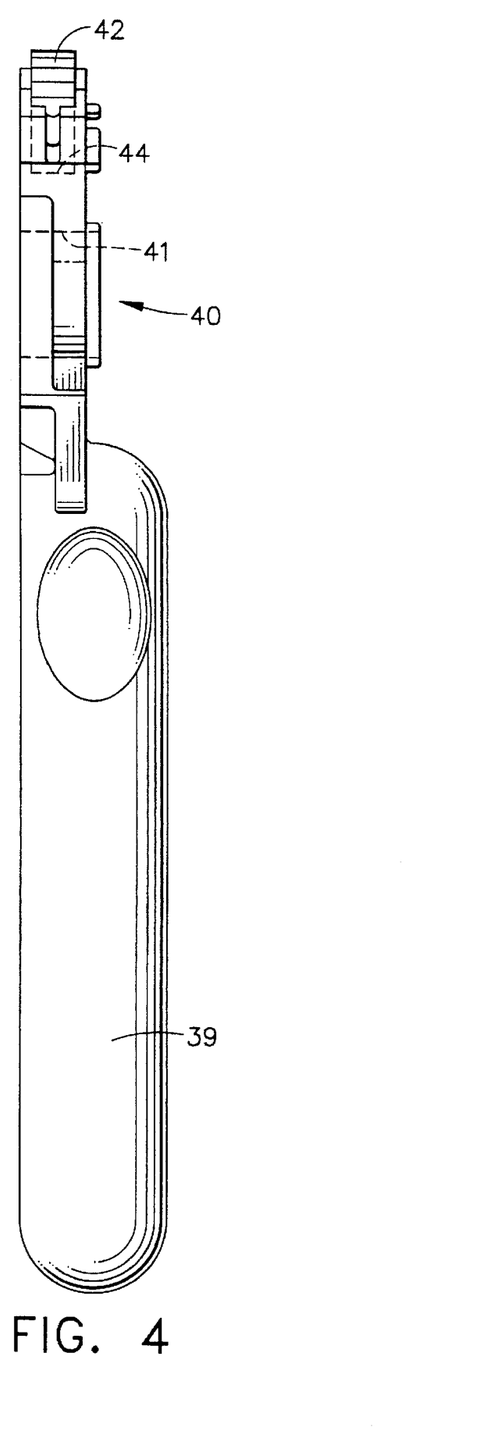
FIG. 4 is a front elevation view of the clamping trigger of FIG. 2.
Figure 5:
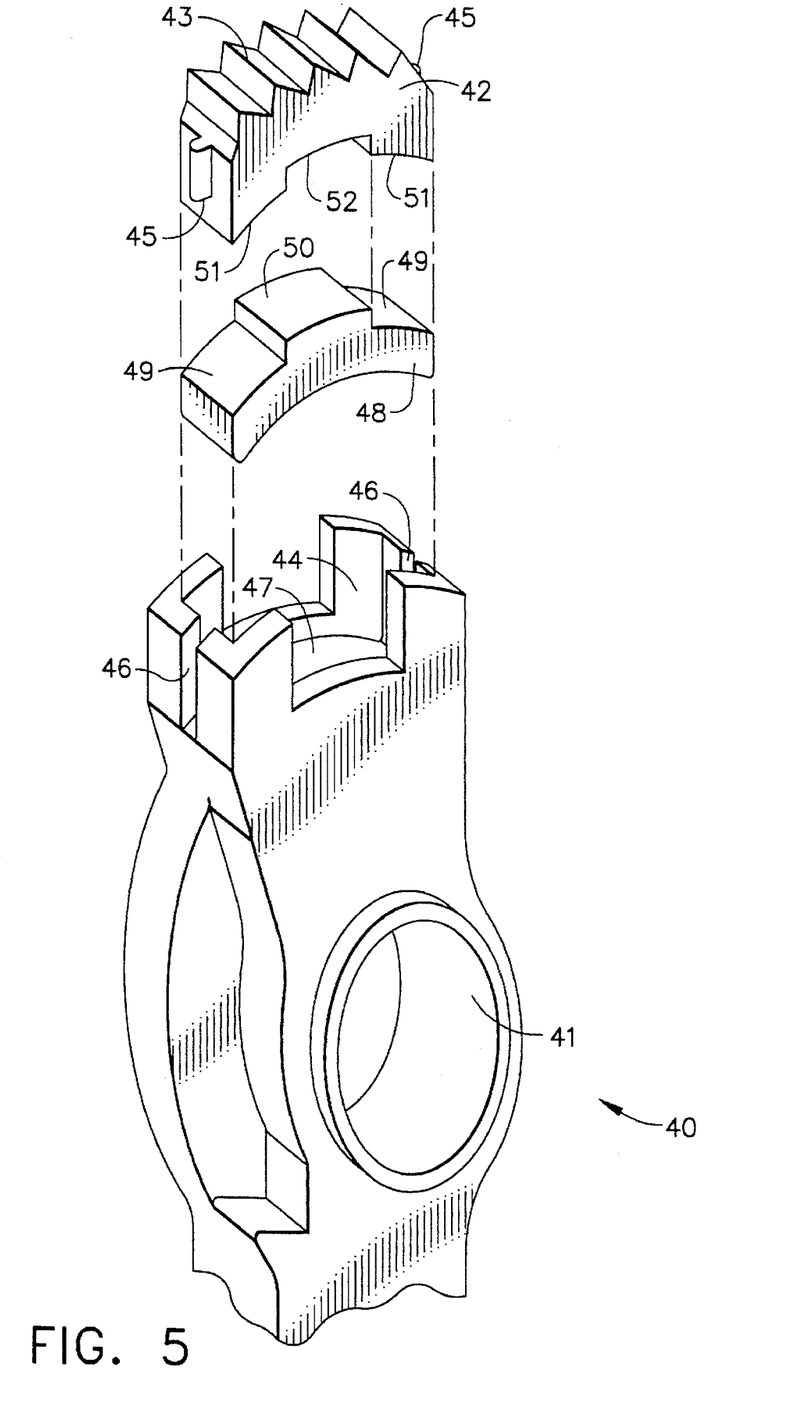
FIG. 5 is an exploded perspective view of the mounting portion of the clamping trigger of FIGS. 2 and 3.

Referring now to FIGS. 3–5, there is illustrated the particular component parts of the surgical instrument of this invention in one preferred embodiment which can be used in connection with, for example, the endocutter depicted in FIGS. 1 and 2. The clamping trigger has a gripping portion 39 which the user squeezes during operation of the instrument, and a mounting potion 40. The mounting portion includes a hole 41 for pivotally mounting the clamping trigger on a boss protruding within the frame (not shown). A pinion 42 having a plurality of gear teeth 43 is mounted to the distal end of the mounting portion of the clamping trigger. The distal end of the mounting portion has a pinion pocket 44 for receiving the pinion. To facilitate the securement of the pinion to the pinion pocket, the pinion has a set of end tabs 45 which are received in a mating pair of tab slots 46 displayed on the pinion pocket.

Importantly, sandwiched between the floor 47 of the pinion pocket and the pinion is an elastomeric spring 48. The elastomeric spring sits on the floor and fits within the pinion pocket. The elastomeric spring has a pair of shoulders 49 separated by a ledge 50. Correspondingly, the pinion has a pair of legs 51 separated by an indentation 52. The pair of legs of the pinion fit inside the pinion pocket and sit on the pair of shoulders of the elastomeric spring. Correspondingly, the ledge of the elastomeric spring fills the space created by the indentation of the pinion.

The elastomeric spring can be composed of ethylene propylene (EPDM), neoprene, silicone rubber, latex rubber or several other similar elastomeric materials. It can be made by standard rubber molding techniques. The spring element may also be a metallic compression spring such as a coil spring or leaf spring. Alternatively, the spring may be composed of any other material which exhibits a compressive stiffness.

Figure 6:
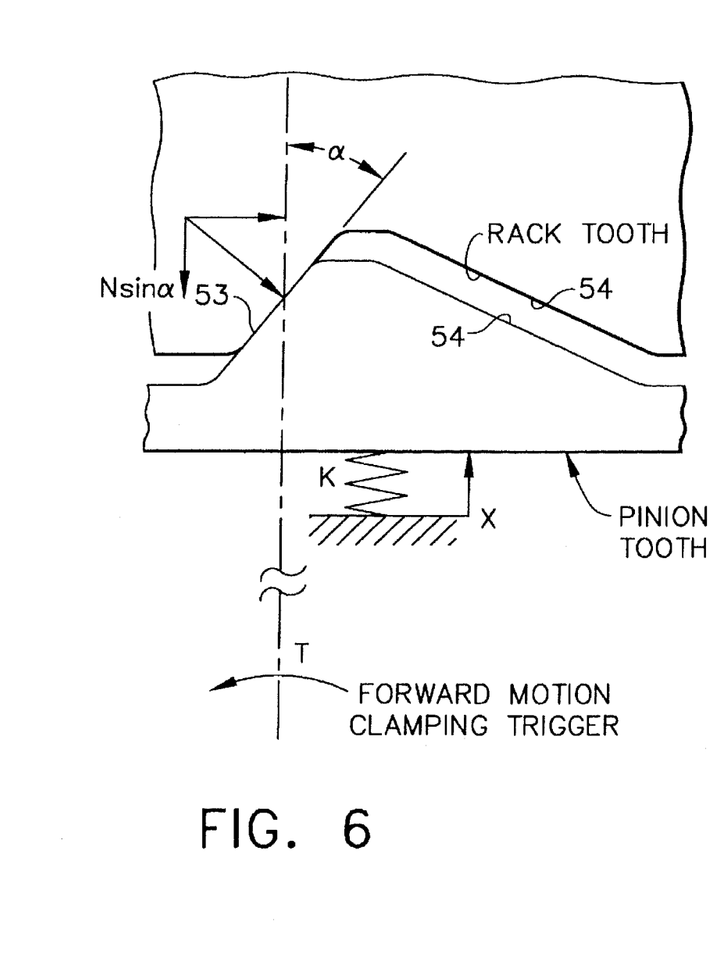
FIG. 6 is a force diagram illustrating the forces present when the engaging element is resiliently biased against the actuator during closure of the clamping trigger.

The elastomeric spring provides an upwardly biasing force against the pinion, and correspondingly, against its associated rack which translates the rotational movement of the clamping trigger into the reciprocating longitudinal movement of the actuator. Specifically, FIG. 6 depicts the interaction between any given tooth of the pinion against the rack on the actuator. The rack incorporates a set of gear teeth in offset relationship relative to the set of gear teeth of the pinion to provide a meshing relationship between the teeth of the rack and pinion. As illustrated in FIG. 6, each tooth of the rack and pinion has a pushing surface 53 and a resetting surface 54. As the clamping trigger is pivoted toward the palm grip handle, the pushing surface of any given pinion tooth engages a corresponding pushing surface of a rack tooth. This interaction causes pressure to be applied against the resilient elastomeric spring. If the load applied to the clamping trigger exceeds a threshold level, then the pressure exerted on the elastomeric spring is so great that the corresponding pushing surfaces of the rack and pinion will no longer be in contact with each other. At this point, greater loads cannot be applied to the component parts of the instrument because the pinion can no longer translate its arcuate motion into the longitudinal motion of the actuator. When this event occurs, a reset condition is established as illustrated in FIG. 6.

Figure 7:
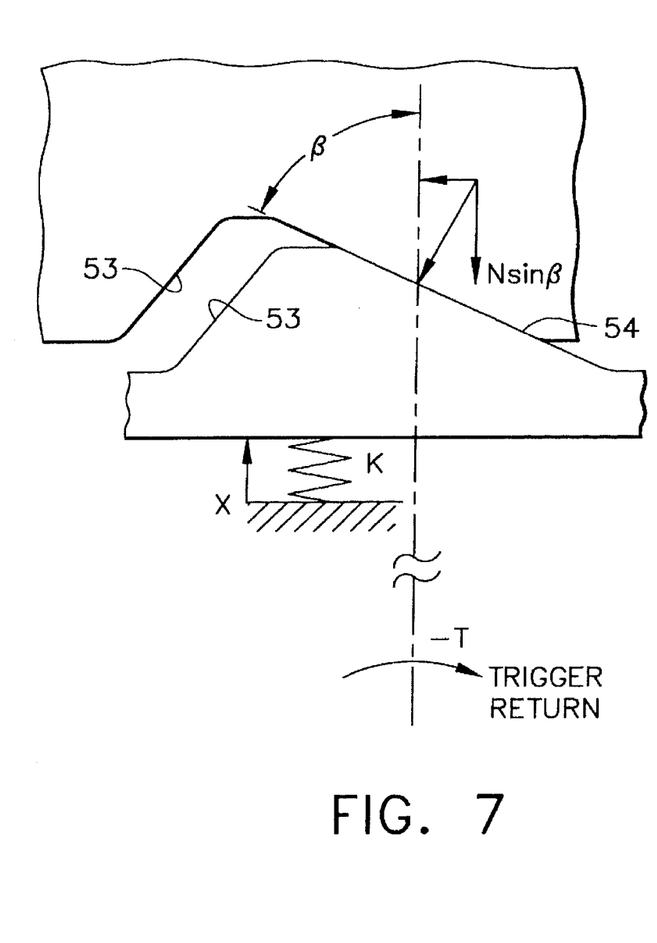
FIG. 7 is a force diagram illustrating the forces present when the engaging element is resiliantly biased away from the actuator during opening of the clamping trigger.

Referring to FIG. 6 in more detail, it depicts the governing forces involved during the forward stroke of the clamping trigger. The force imparted by the pinion gear tooth of the trigger at some instance in time is perpendicular, i.e. normal, to the point of contact between the pinion and rack gear teeth. The horizontal component of this normal force causes forward motion of the rack. The vertical component, Nsinα, is resisted by the spring with spring rate, K (lb./in.) This is a function of the elastomer durometer rating of the spring and is relatively linear over a small range of deflection, x (in.). When the product, K times x (ib./in.), is exceeded by the vertical force component, Nsinα, the gear teeth will begin to disengage. This will also be the case when the trigger moves in the opposite direction as shown in FIG. 7.

In a particularly preferred embodiment, each of the teeth of the rack and pinion are asymmetrical. Specifically, the pushing surface 53 of each tooth has a substantially greater slope than the resetting surface 54. As a result, the angle "β" (FIG. 7), is much greater than α (FIG. 6). Therefore, the trigger pinion is a much more effective "wedge" in the return direction, and the gear teeth will disengage at a much smaller force of the trigger imparted on the rack. Since the force needed to fire staples and cut the tissue in an endocutter is more than what is needed to return the trigger, this big difference in horizontal force transfer is allowable. If the teeth slip during forward motion, the trigger can be reset at a much smaller force, either automatically by the return spring (see FIGS. 1 and 2, frame assembly spring 30) or manually by hand.

Figure 8:
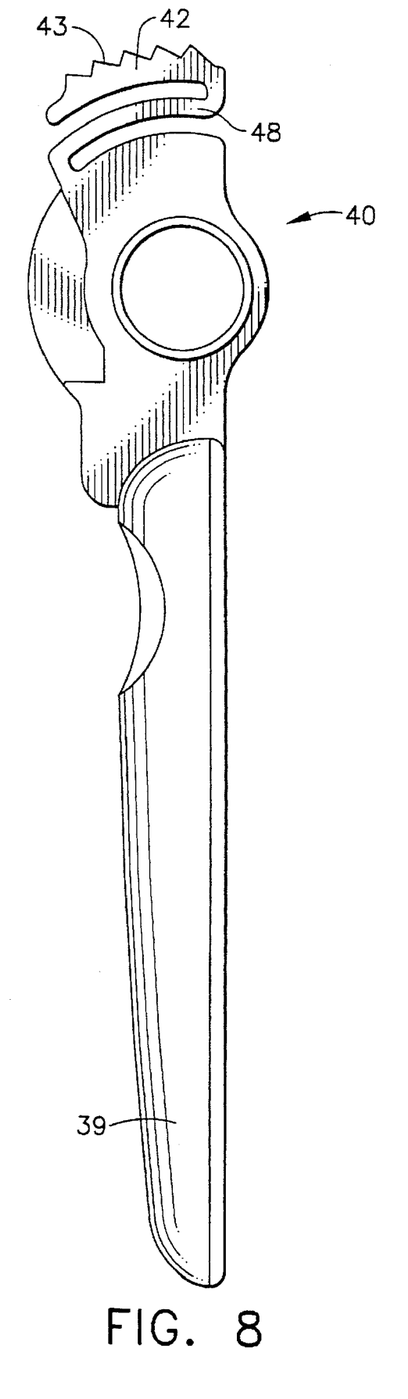
FIG. 8 is a side elevation of an alternative clamping trigger constructed in accordance with the invention.
Figure 9:
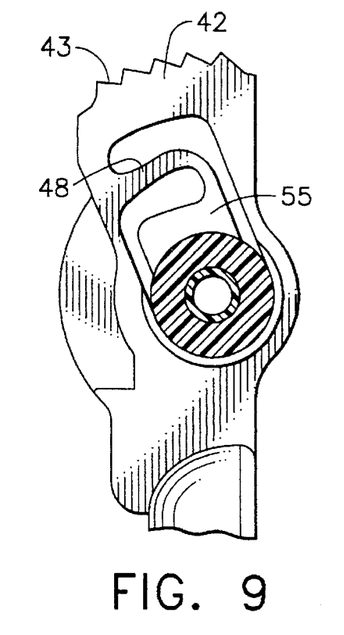
FIG. 9 is a side elevation of another alternative clamping trigger constructed in accordance with the invention.
Figure 10:
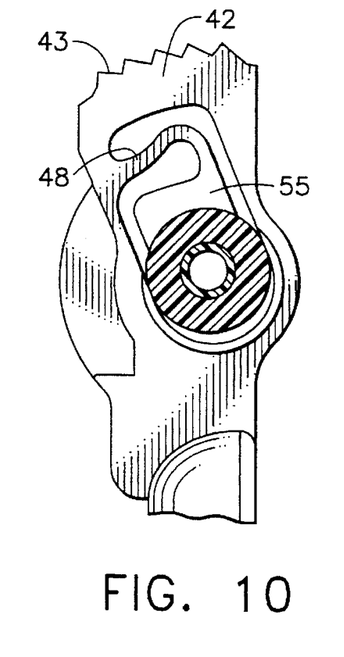
FIG. 10 is a partial side elevation of the clamping trigger of FIG. 9 in its disengaged position.
Figure 11:
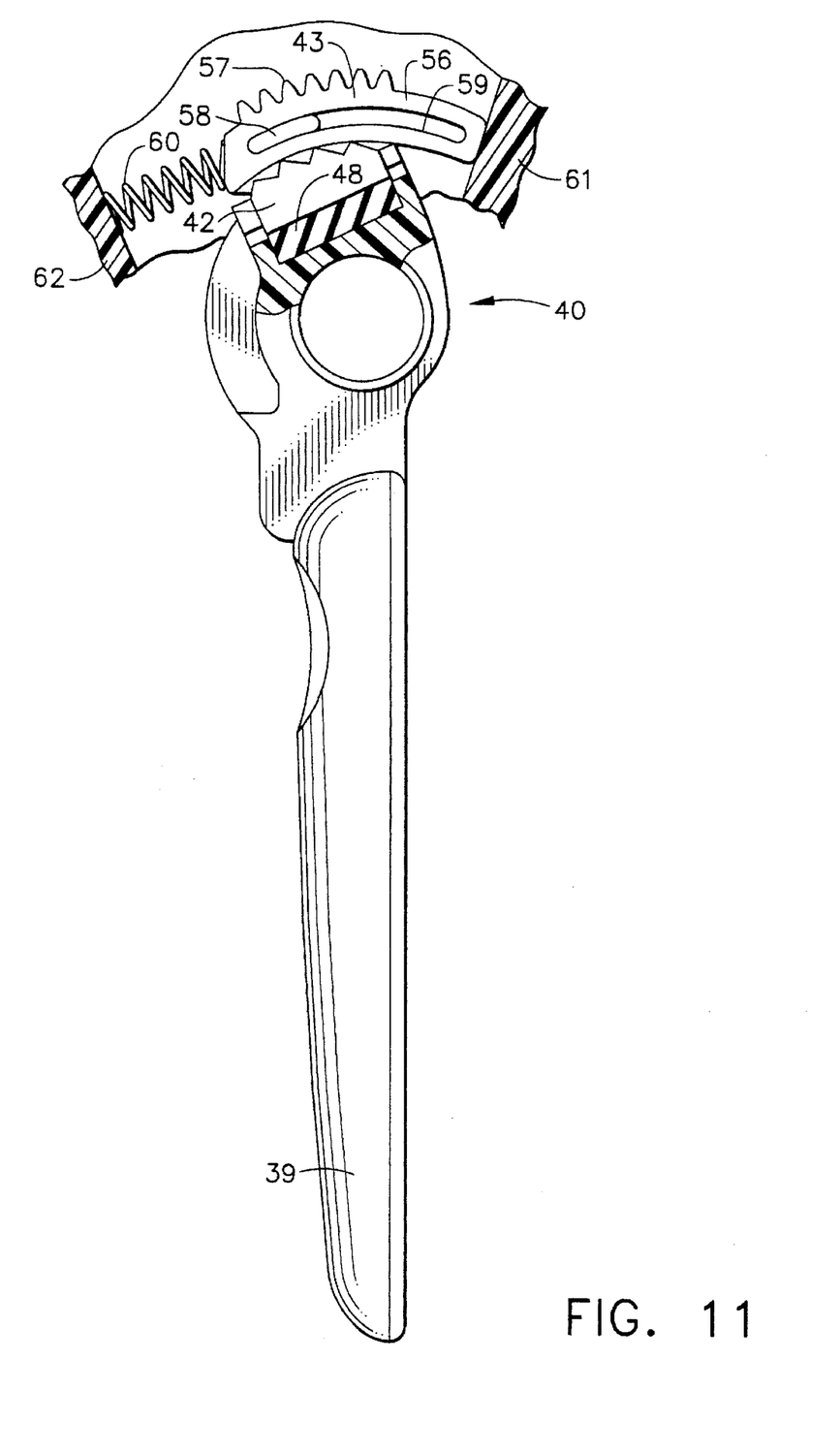
FIG. 11 is a side elevation of a further alternative clamping trigger constructed in accordance with the invention.

Alternative embodiments for the pinion, spring and clamping trigger of the surgical instrument of this invention are illustrated in FIGS. 8–11. As shown in FIG. 8, the pinion and spring can be integral with the clamping trigger. FIGS. 9 and 10 illustrate a flexible mounting shoe 55 which is integral with the mounting portion of the clamping trigger. When the flexible mounting shoe is displaced upon excessive loading, which arises from pivotal movement of the clamping trigger, the integral spring is capable of flexing to releasably bias the pinion. Referring to FIG. 11, the pinion is engaged to a slotted rack 56 with a second set of pinion gear teeth 57. The slotted rack is fixed to the frame using a body boss 58 protruding through the slot 59. When the clamping trigger is squeezed, the slotted rack translates the arcuate motion of the clamping trigger into longitudinal motion of the actuator. The slotted rack must overcome the resistance generated from a reset spring 60. If a load is applied exceeding a threshold level, then a corresponding threshold resistance is realized from the reset spring and the compressive forces exerted on the elastomeric spring 48 will release the pinion from the actuator rack (not shown). The slotted pinion rack rests on a first body stop 61 at a first end of the slotted pinon rack. The opposite end of the slotted pinion rack is fixed to the reset spring, which in turn is attached to a second body stop 62. Reset spring 60 resets the teeth 43 to their "home" position if the teeth slip during the forward stroke of clamping trigger 39. This embodiment allows the trigger pinion to remain fully engaged with the gear teeth of the actuator or rack so as not to affect the timing or load transfer capability of those teeth.

Although this invention has been described in connection with its most preferred embodiment, numerous additional embodiments would be readily apparent to those skilled in the art. Therefore, these additional embodiments would fall within the scope and spirit of the claimed invention. For example, and by way of example only, the beneficial features of the surgical instrument of this invention may be used not only in connection with endoscopic linear cutters, but also other instruments as well. Such instruments may include, but are not limited to, various open and endoscopic instruments such as graspers, forceps and linear staplers.

What is claimed is:

1. A surgical instrument capable of clamping bodily tissue during a surgical procedure, said instrument comprising:

a) a frame;

b) a shaft extending from said frame, said shaft having a distal end;

c) an end effector connected to said shaft distal end, said end effector including first and second opposed jaws movable from an open position, wherein said jaws are spaced apart from each other to a closed position for clamping said tissue between said jaws;

d) a clamping trigger movably mounted to said frame, said clamping trigger having a gripping portion at a first end of said trigger and a mounting portion at an opposite end, said clamping trigger movable from a first position to a second position;

e) a resilient spring element fixed to said mounting portion of said clamping trigger;

f) an actuator reciprocatable within said frame in response to movement of said clamping trigger, said actuator operatively connected to said jaws through said shaft; and g) an engaging element attached to said resilient spring element, said engaging element releasably biased by said resilient spring element against said actuator;

wherein when said engaging element is biased against said actuator, movement of said clamping trigger from said first to said second positions causes said actuator to reciprocate in a forward direction so as to move said jaws from said open to said closed positions, and when said engaging element is released by said resilient spring element from biasing against said actuator, movement of said clamping trigger from said first to said second positions no longer causes said actuator to reciprocate in a forward direction for corresponding movement of said jaws.

2. The instrument of claim 1 wherein said actuator includes an actuator rack, and said engaging element is a pinion releasably interacting with said rack.

3. The instrument of claim 2 wherein said rack and pinion have a plurality of opposed teeth offset from each other so that said opposed teeth from said rack and pinion mesh with each other, and each tooth of said rack and pinion has a pushing surface and a resetting surface, said pushing surface having a slope substantially greater than that of said resetting surface, wherein when said clamping trigger moves from said first to said second positions, said pushing surfaces of said pinion teeth apply force against said pushing surfaces of said rack teeth.

4. The instrument of claim 3 wherein said resilient spring element is an elastomeric spring or a metallic compression spring.

5. The instrument of claim 4 wherein said mounting portion of said clamping trigger has a distal end, and said resilient spring element is attached to said distal end of said mounting portion.

6. The instrument of claim 2 wherein said mounting portion of said clamping trigger has a distal end, and said resilient spring element and said pinion are integral with said distal end of said mounting portion.

7. The instrument of claim 1 wherein said frame includes a palm grip handle, and said clamping trigger is pivotally mounted to said frame for rotational movement from said first position spaced from said palm grip handle to said second position adjacent said palm grip handle.

8. A surgical instrument capable of manipulating bodily tissue during a surgical procedure, said instrument comprising:

a) a frame;

b) a shaft extending from said frame, said shaft having a distal end;

c) an end effector connected to said shaft distal end, said end effector including a manipulating member which upon actuation clamps, fastens or cuts said bodily tissue;

d) a trigger movably mounted to said frame, said trigger having a gripping portion at a first end of said trigger and a mounting portion at an opposite end, said trigger movable from a first position to a second position;

e) a resilient spring element fixed to said mounting portion of said trigger;

f) an actuator reciprocatable within said frame in response to movement of said trigger, said actuator operatively connected to said jaws through said shaft; and g) an engaging element attached to said resilient spring element, said engaging element releasably biased by said resilient spring element against said actuator;

wherein when said engaging element is biased against said actuator, movement of said trigger from said first to said second positions causes said actuator to reciprocate in a forward direction so as to actuate said manipulating member, and when said engaging element is released by said resilient spring element from biasing against said actuator, movement of said trigger from said first to said second positions no longer causes said actuator to reciprocate in a forward direction so as to actuate said manipulating member.

9. The instrument of claim 8 wherein said actuator includes an actuator rack, and said engaging element is a pinion releasably interacting with said rack.

10. The instrument of claim 9 wherein said rack and pinion have a plurality of opposed teeth offset from each other so that said opposed teeth from said rack and pinion mesh with each other, and each tooth of said rack and pinion has a pushing surface and a resting surface, said pushing surface having a slope substantially greater than that of said resetting surface, wherein when said clamping trigger moves from said first to said second positions, said pushing surfaces of said pinion teeth apply force against said pushing surfaces of said rack teeth.

11. The instrument of claim 10 wherein said resilient spring element is an elastomeric spring or a metallic compression spring.

12. The instrument of claim 11 wherein said mounting portion of said trigger has a distal end, and said resilient spring is attached to said distal end of said mounting portion.

13. The instrument of claim 12 wherein said mounting portion of said trigger has a distal end, and said resilient spring element and said pinion are integral with said distal end of said mounting portion.

14. The instrument of claim 13 wherein said frame includes a palm grip handle, and said trigger is pivotally mounted to said frame for rotational movement from said first position spaced from said palm grip handle to said second position adjacent said palm grip handle.

\* \* \* \* \*